(12) United States Patent
Shi et al.

(10) Patent No.: US 7,875,598 B2
(45) Date of Patent: Jan. 25, 2011

(54) COMPOSITIONS USEFUL FOR THE TREATMENT OF MICROBIAL INFECTIONS

(75) Inventors: Wenyuan Shi, Los Angeles, CA (US); Li Chen, Los Angeles, CA (US); Qing-yi Lu, Los Angeles, CA (US); David Heber, Los Angeles, CA (US); Maxwell H. Anderson, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 1317 days.

(21) Appl. No.: 10/795,554

(22) Filed: Mar. 4, 2004

(65) Prior Publication Data

US 2006/0135498 A1    Jun. 22, 2006

(51) Int. Cl.
*A61K 31/58* (2006.01)
*A61K 31/70* (2006.01)
*A01N 43/04* (2006.01)
*C07J 71/00* (2006.01)

(52) U.S. Cl. .......................... 514/172; 514/27; 540/17
(58) Field of Classification Search ................. 524/26; 514/172, 27; 540/17
See application file for complete search history.

(56) References Cited

U.S. PATENT DOCUMENTS

| 4,150,116 | A | 4/1979 | Taubman et al. |
|---|---|---|---|
| 4,250,262 | A | 2/1981 | Taubman et al. |
| 4,324,782 | A | 4/1982 | Beck |
| 4,442,085 | A | 4/1984 | Colman et al. |
| 4,448,768 | A | 5/1984 | Colman et al. |
| 4,521,513 | A | 6/1985 | Russell |
| 4,671,958 | A | 6/1987 | Rodwell et al. |
| 4,693,888 | A | 9/1987 | Miyahara et al. |
| 4,725,428 | A | 2/1988 | Miyahara et al. |
| 5,057,313 | A | 10/1991 | Shih et al. |
| 5,281,524 | A | 1/1994 | Horikoshi et al. |
| 5,332,567 | A | 7/1994 | Goldenberg |
| 5,352,446 | A | 10/1994 | Lehner |
| 5,352,450 | A | 10/1994 | Koga et al. |
| 5,439,680 | A | 8/1995 | Horikoshi et al. |
| 5,518,721 | A | 5/1996 | Lehner et al. |
| 5,612,031 | A | 3/1997 | Lehner et al. |
| 5,645,835 | A | 7/1997 | Fell, Jr. et al. |
| 5,646,119 | A | 7/1997 | Oppenheim et al. |
| 5,672,351 | A | 9/1997 | Chikindas et al. |
| 5,686,075 | A | 11/1997 | Taubman et al. |
| 5,726,293 | A | 3/1998 | Seed |
| 5,851,527 | A | 12/1998 | Hansen |
| 5,874,068 | A | 2/1999 | Engelman et al. |
| 5,875,798 | A | 3/1999 | Petrus |
| 5,877,293 | A | 3/1999 | Adair et al. |
| 5,891,422 | A | 4/1999 | Pan et al. |
| 5,910,573 | A | 6/1999 | Pluckthun et al. |
| 5,981,726 | A | 11/1999 | Pastan et al. |
| 6,046,037 | A | 4/2000 | Hiatt et al. |
| 6,183,744 | B1 | 2/2001 | Goldenberg |
| 6,197,299 | B1 | 3/2001 | Dohlsten et al. |
| 6,231,857 | B1 | 5/2001 | Shi et al. |
| 6,254,856 | B1 | 7/2001 | Tsuchiya |
| 6,309,835 | B1 | 10/2001 | Iyer et al. |
| 6,346,267 | B1 | 2/2002 | Fry et al. |
| 6,492,328 | B2 | 12/2002 | Lehrer et al. |
| 6,559,176 | B1 | 5/2003 | Bassler et al. |
| 6,673,900 | B2 | 1/2004 | Rowe |
| 2002/0068066 | A1 | 6/2002 | Shi et al. |
| 2002/0102316 | A1 | 8/2002 | Weissman |
| 2003/0143234 | A1 | 7/2003 | Shi et al. |
| 2003/0171421 | A1 | 9/2003 | Davies et al. |
| 2003/0186916 | A1 | 10/2003 | Yu et al. |
| 2003/0211185 | A1 | 11/2003 | Alexis |
| 2003/0228379 | A1* | 12/2003 | Shi et al. .................... 424/725 |
| 2003/0229000 | A1 | 12/2003 | Merritt et al. |
| 2004/0023254 | A1 | 2/2004 | Fuhrmann et al. |
| 2004/0052814 | A1 | 3/2004 | Shi et al. |
| 2004/0137482 | A1 | 7/2004 | Eckert et al. |
| 2004/0147595 | A1 | 7/2004 | Kjelleberg et al. |
| 2004/0234662 | A1* | 11/2004 | Ben-Yehoshua ............ 426/532 |
| 2005/0255128 | A1 | 11/2005 | Merritt et al. |
| 2005/0288229 | A1 | 12/2005 | Sindrey et al. |

(Continued)

FOREIGN PATENT DOCUMENTS

CN    1415301    5/2003

(Continued)

OTHER PUBLICATIONS

Deng et al. "Synthesis of three diosgenyl saponins: dioscin, polyphyllin D, and balanitin 7", Carbohydrate Research, 1999, vol. 317, pp. 53-62.*

(Continued)

*Primary Examiner*—Sreeni Padmanabhan
*Assistant Examiner*—Kendra D Carter
(74) *Attorney, Agent, or Firm*—Morgan, Lewis & Bockius LLP; Annette S. Parent

(57) ABSTRACT

The present invention is based on the discovery that certain chemical compounds isolated from Chinese medicinal herbs are useful as anti-microbial agents, e.g., anti-bacterial agents, anti-fungal agents, and the like. In particular, the present invention provides compositions useful for treating microbial infections such as, for example, oral microbial infections, including periodontal disease and dental caries.

11 Claims, No Drawings

U.S. PATENT DOCUMENTS

2006/0135498 A1     6/2006    Shi et al.

FOREIGN PATENT DOCUMENTS

| | | |
|---|---|---|
| EP | 0 140 498 A1 | 5/1985 |
| EP | 0 334 467 A2 | 9/1989 |
| GB | 2 143 829 A | 2/1985 |
| JP | 77021571 B * | 6/1977 |
| JP | 2-177899 A | 7/1990 |
| JP | 5-227916 A | 9/1993 |
| JP | 6-122633 A | 5/1994 |
| JP | 2000-198724 | 7/2000 |
| WO | WO 92/22653 A1 | 12/1992 |
| WO | WO 94/09817 A1 | 5/1994 |
| WO | WO 99/58141 A1 | 11/1999 |
| WO | WO 00/11037 A1 | 3/2000 |
| WO | WO 01/85664 A2 | 11/2001 |
| WO | WO 01/85664 A3 | 11/2001 |
| WO | WO 02/15931 A1 | 2/2002 |
| WO | WO 02/22686 A2 | 3/2002 |
| WO | WO 02/22686 A3 | 3/2002 |
| WO | WO 02/102975 A2 | 12/2002 |
| WO | WO 02/102975 A3 | 12/2002 |
| WO | WO 2004/028519 | 4/2004 |

OTHER PUBLICATIONS

Hufford et al. "Antifungal activity of *Trillium grandiflorum* constituents" Journal of Natural Products, Jan.-Feb. 1988, vol. 51, No. 1, pp. 94-98.*

Haraguchi et al. "Mode of the Antifungal Action of Chrysodin in *Candida albicans*" Agric. Biol. Chem., 1990, vol. 54, No. 9, pp. 2417-2422.*

Nakamoto et al. "In vitro study on the effects of trial dinture cleansers with berberine hydrochloride" J Prosthet Dent, 1995, vol. 73, pp. 530-533.*

Tan et al. "Acyl secoiridoids and antifungal constituents from *Gentiana macrophylla*" Phytochemistry, 1996, vol. 42., No. 5, pp. 1305-1313.*

International Search Report.

Arakawa, T. et al., "Plants are not just Passive Creatures!" *Nature Medicine*, May 1998, vol. 4, No. 5, pp. 550-551.

Barbeau, J. et al., "Biofilms, Infectious Agents, and Dental Unit Waterlines: A Review," *Can. J. Microbiol.*, 1998, vol. 44, pp. 1019-1028.

Bassler, B.L., "How Bacteria Talk to Each Other: Regulation of Gene Expression by Quorum Sensing," *Current Opinion in Microbiology*, 1999, vol. 2, pp. 582-587.

Bhagwat, S.P. et al., "Effects of Mutating Putatuve Two-Component Systems on Biofilm Formation by *Streptococcus mutans* UA159," *FEMS Microbiology Letters*, 2001, vol. 205, pp. 225-230.

Blondelle, S.E. et al., "Combinatorial Libraries: A Tool to Design Antimicrobial and Antifungal Peptide Analogues Having Lytic Specificities for Structure-Activity Relationship Studies," *Biopolymers*, 2000, vol. 55, pp. 74-87.

Bowie, J.U. er al., "Deciphering the Message in Protein sequences: tolerance to Amino Acid Substitutions," *Science*, Mar. 6, 1990, vol. 247, pp. 1306-1310.

Brogden, K.A. et al., "Antimicrobial Peptides in Animals and Their Role in Host Defences," *International Journal of Antimicrobial Agents*, 2003, vol. 22, pp. 465-478.

Brogden, K.A., "Antimicrobial Peptides: Pore Formers or Metabolic Inhibitors in Bacteria?" *Nature Reviews Microbiology*, Mar. 2005, vol. 3, pp. 238-250.

Chen, P. et al., "The Specific Genes for Lantobiotic Mutacin II Biosynthesis in *Streptococcus mutans*, T8 are Clustered and Can be Transferred en Bloc," *Applied and Environmental Microbiology*, Mar. 1999, vol. 65, No. 3, pp. 1356-1360.

Chen, X. et al., "Structural Identification of the Bacterial Quorum-Sensing Signal Containign Boron," *Nature*, Jan. 31, 2002, vol. 415, pp. 545-549.

Chung, W.O. et al., "Signaling Systems in *Porphyromonas gingivalis* Based on a LuxS Protein," *Journal of Bacteriology*, Jul. 2001, vol. 183, No. 13, pp. 3903-3909.

Davey, M.E. et al., "Microbial Biofilms: Form Ecology to Molecular Genetics," *Microbiology and Molecular Biology Reviews*, Dec. 2000, vol. 64, No. 4, pp. 847-867.

Davies, D.G. et al., "The Involvement of Cell-to-Cell Signals in the Development of a Bacterial Biofilm," *Science*, Apr. 10, 1998, vol. 280, pp. 295-298.

Day, W.A., Jr. et al., "*Shigella flexneri* LuxS Quorum-Sensing System Modulates *virB* Expression but is Not Essential for Virulence," *Infection and Immuity*, Jan. 2001, vol. 69, No. 1, pp. 15-23.

DeSlouches, B. et al., "De Novo Generation of Cationic Antimicrobial Peptides: Influence of Length and Tryptophan Substitution on Antimicrobial Activity," *Antimicrobial Agents and Chemotherapy*, Jan. 2005, vol. 49, No. 1, pp. 316-322.

Diamond, G., "Nature's Antibiotics: The Potential of Antimicrobial Peptides as New Drugs," *Biologist*, 2001, vol. 48, No. 5, pp. 209-212.

Dunny, G.M. et al., "Cell-Cell Communication in Gram-Positive Bacteria," *Annu. Rev. Microbiol.*, 1997, vol. 51, pp. 527-564.

European Examination Report mailed on Feb. 21, 2007, for EP Application No. EP 02752402.4 filed on Jul. 17, 2002, 6 pages.

European Examination Report mailed on May 16, 2008, for EP Application No. 02752402.4 filed on Jul. 17, 2002, 7 pages.

European Search Report mailed on Sep. 9, 2005, for EP Application No. EP 02752404.4, 4 pages.

Everhart, D.L. et al., "Dental Caries Vaccines: Some Problems Solved?" *Microbiological Science*, 1985, vol. 2, No. 10, pp. 312-313.

Fong, K.P. et al., "Intra- and Interspecies Regulation of Gene Expression by *Actinobacillus actinomycetemcomitans* LuxS," *Infection and Immunity*, Dec. 2001, vol. 69, No. 12, pp. 7625-7634.

Forsyth, M.H. et al., "Intercellular Communication in *Helibacter pylori*: *luxS* is Essential for the Production of an Extracellular Signaling Molecule," *Infection and Immunity*, Jun. 2000, vol. 68, No. 6, pp. 3193-3199.

Fortney, K. et al., "*Haemophilus ducreyi* is Susceptible to Protegrin," *Antimicrobial Agents and Chemotherapy*, Oct. 1998, vol. 42, No. 10, pp. 2690-2693.

Frias, J. et al., "Periodontal Pathogens Produce Quorum Sensing Signal Molecules," *Infection and Immunity*, May 2001, vol. 69, No. 5, pp. 3431-3434.

Fuqua, C. et al., "Self Perception in Bacteria: Quorum Sensing with Acylated Homoserine Lactones," *Current Opinion in Microbiology*, 1998, vol. 1, pp. 183-189.

Ganz, T. et al., "Antimicrobial Peptides in Innate Immunity," Chapter 11 in *Development of Novel Antimicrobial Agents: Emerging Strategies*, 2001, Horizon Scientific Press: Wymondham, England, pp. 139-147.

Gao, H. et al., "Hydrophobic Contribution Constants of Amino Acid Residues to the Hydrophobicities of Oligopeptides," *Pharmaceutical Research*, 1995, vol. 12, No. 9, pp. 1279-1283.

Gazi, M.I., "Monoclonal Antibodies in Dentistry," *British Dental Journal*, Dec. 6, 1986, vol. 161, No. 11, pp. 399-405.

Giacometti, A. et al., "Antimicrobial Activity of Polycationic Peptides," *Peptides*, 1999, vol. 20, pp. 1265-1273.

Greenspan, N.S. et al., "Defining Epitopes: It's Not Easy as it Seems," *Nature Biotechnology*, Oct. 1999, vol. 17, pp. 936-937.

Grigoriev, P.A. et al., "Differences in Membrane Pore Formation by Peptaibols," *Journal of Peptide Science*, 2003, vol. 9, pp. 763-768.

Groenink, J. et al., "Cationic Amphipathic Peptides, Derived from Bovine and Human Lactoferrins, with Antimicrobial Activity Against Oral Pathogens," *FEMS Microbiology Letters*, 1999, vol. 179, pp. 217-222.

Hancock, R.E.W., "Cationic Peptides: Effectors in Innate Immunity and Novel Antimicrobials," *The Lancet Infectious Diseases*, Oct. 2001, vol. 1, pp. 156-164.

Hazlett, K.R.O. et al., "Inactivation of the *gbpA* Gene of *Streptococcus mutans* Alters Structural and Functional Aspects of Plaque Biofilm Which are Compensated by Recombincation of the *gtfB* and *gtfC* Genes," *Infection and Immunity*, Aug. 1999, vol. 67, No. 8, pp. 3909-3914.

Helmerhost, E.J. et al., "Synthetic Histatin Analogues with Broad-Spectrum Antimicrobial Activity," *Biochem. J.*, 1997, vol. 326, pp. 39-45.

Hong, S.Y. et al., "The Effect of Charge Increase on the Specificity and Activity of a Short Antimicrobial Peptide," *Peptides*, 2001, vol. 22, pp. 1669-1674.

Huang, H.W. et al., "Molecular Mechanism of Peptide-Induced Pores in Membranes," *Physical Review Letters*, May 14, 2004, vol. 92, No. 19, pp. 198304-1-198304-4.

Huber, B. et al., "The *Cep* Quorum-Sensing System of *Burkholderia cepacia* H111 Controls Biofilm Formation and Swarming Motility," *Microbiology*, 2001, vol. 147, pp. 2517-2528.

International Search Report mailed on Jan. 2, 2003, for PCT Application No. PCT/US02/22695, 4 pages.

International Search Report mailed on Sep. 24, 2003, for PCT Application No. PCT/US02/18692, 2 pages.

International Search Report mailed on Nov. 27, 2007, for PCT Application No. PCT/US06/34109, 3 pages.

Joyce, E.A. et al., "Evidence for a Signaling System in *Heliobacter pylori*: Detection of a *luxS*-Encoded Autoinducer," *Journal of Bacteriology*, 2000, vol. 182, No. 13, pp. 3638-3643.

Keene, H.J. et al., "Relationship of *Streptococcus mutans* Carrier Status to the Development of Carious Lesions in Initially Cariesfree Recruits," *J. Dent. Res.*, Oct. 1974, vol. 53, No. 5, p. 1295.

Kiyota, T. et al., "Design and Synthesis of Amphiphilic α-Helical Model Peptides with Systematically Varied Hydrophobic-Hydrophilic Balance and Their Interaction with Lipid- and Bio-Membranes," *Biochemistry*, 1996, vol. 35, No. 40, pp. 13196-13204.

Kobayashi, I. et al., "Biological Behavior of Human Dental Pulp Cells in Response to Carious Stimuli Analyzed by PCNA Immunostaining and AgNOR Staining," *Caries Research*, 1996, vol. 30, No. 3, pp. 225-230.

Kolenbrander, P.E. et al., "Intergeneric Coaggregation of Oral *Treponema* spp. with *Fusobacterium* spp. and Intrageneric Coaggregation Among *Fusobacterium* spp.," *Infection and Immunity*, Dec. 1995, vol. 96, No. 12, pp. 4584-4588.

Kolenbrander, P.E. "Oral Microbial Communities: Biofilms, Interactions, and Genetic Systems," *Annu. Rev. Microbiol.*, 2000, vol. 54, pp. 413-437.

Kuby, J., *Immunology*, 2nd Edition, W.H. Freeman and Company: New York, NY, 1994, pp. 19-20.

Lee, K-H., "Development of Short Antimicrobial Peptides Derived from Host Defense Peptides or by Combinatorial Libraries," *Current Pharmaceutical Design*, 2002, vol. 8, No. 9, pp. 795-813.

Leher, R.I. et al., "Defensins of Vertebrate Animals," *Current Opinion in Immunology*, 2002, vol. 14, pp. 96-102.

Lehner, T. et al., "Local Passive Immunization by Monoclonal Antibodies Against Streptococcal Antigen I/II in the Prevention of Dental Caries," *Infection and Immunity*, Dec. 1985, vol. 50, No. 3, pp. 796-799.

Lehner, T. et al., "A Mechanism of Passive Immunization with Monoclonal Antibodies to a 185,000 $M_r$ Streptococcal Antigen," *Advances in Experimental Medicine and Biology (Genetically Engineered Vaccines)*, 1992, vol. 327, pp. 151-163.

Li, P. et al., "An Antimicrobial Peptide Gene Found in the Male Reproductive System of Rats," *Science*, Mar. 2, 2001, vol. 291, pp. 1783-1785.

Li, Y.H. et al., "Nature Genetic Transformation of *Stretococcus mutans* Growning in Biofilms," *J. Bacteriol.*, Feb. 2001, vol. 183, No. 3, pp. 897-908.

Li, Y-H. et al., "A Quorum-Sending System Essential for Induction of Genetic Competence in *Streptococcus mutans* is Involved in Biofilm Formation," *Abstracts of the General Meeting of the American Society for Microbiology*, May 2001, vol. 101, Abstract No. J-8, p. 442.

Loo, C.Y. et al., "*Streptococcus gordonii* Biofilm Formation: Identification of Genes that Code for Biofilm Phenotypes," *Journal of Bacteriology*, Mar. 2000, vol. 182, No. 5, pp. 1374-1382.

Lyon, W.R. et al., "Mutation of *luxS* Affects Growth and Virulence Factor Expression in *Streptococcus pyogenese*," *Molecular Microbiology*, 2001, vol. 42, No. 1, pp. 145-157.

Ma, J.K-C. et al., "Use of Monoclonal Antibodies in Local Passive Immunization to Prevent Colonization of Human Teeth by *Streptoccus mutans*," *Infection and Immunity*, May 1987, vol. 55, No. 5, pp. 1274-1278.

Ma, J.K-C. et al., "An Investigation into the Mechanism of Protection by Local Passive Immunization with Monoclonal Antibodies Against *Streptococcis mutans*," *Infection and Immunity*, Oct. 1990, vol. 58, No. 10, pp. 3407-3414.

Ma, J. K-C. et al., " Assembly of Monoclonal Antibodies with IgG1 and IgA Heavy Chain Domains in Transgenic Tobacco Plants," *European Journal of Immunology*, 1994, vol. 24, No. 1, pp. 131-138.

Ma, J. K-C. et al., "Characterization of a Recombinant Plant Monoclonal Secretory Antibody and Preventive Immunotherapy in Humans," *Nature Medicine*, May 1998, vol. 4, No. 5, pp. 601-606.

Marshall, S.A. et al., "Spectrum and Antimicrobial Activity of Alexomycin (PNU-82, 127), a Peptide Compound Projected for Use in Animal Health," *Diagn. Microgiol. Infect. Dis.*, 1999, vol. 33, pp. 181-186.

Mattos-Graner, R.O. et al., "Cloning of the *Streptcpccus mutans* Gene Encoding Glucan Binding Protein B and Analysis of Genetic Diversity and Protein Production in Clinical Isolates," *Infection and Immunity*, Nov. 2001, vol. 69, No. 11, pp. 6931-6941.

Miyasaki, K.T., et al., "β-Sheet Antibiotic Peptides as Potential Dental Therapeutics," *International Journal of Antimicrobial Agents*, 1988, vol. 9, pp. 269-280.

Morrison, S.L. et al., "Chimeric Human Antibody Molecules: Mouse Antigen-Binding Domains with Human Constant Region Domains with Human Constant Region Domains," *Proc. Natl. Acad. Sci. USA*, Nov. 1984, vol. 81, pp. 6851-6855.

Nicolas, P. et al., "Peptides as Weapons Against Microorganisms in the Chemical Defense System of Vertebrates," *Annual Review of Microbiology*, 1995, vol. 49, 19 pages.

Parsek, M.R. et al., "Acyl-homoserine Lactone Quorum Sensing in Gram-negative Bacteria: A Signaling Mechanism Involved in Associations with Higher Organisms," *PNAS*, Aug. 1, 2000, vol. 97, No. 16, pp. 8789-8793.

Penichet, M.L. et al., "Antibody-Cytokine Fusion Proteins for the Therapy of Cancer," *Journal of Immunological Methods*, 2001, vol. 248, pp. 91-101.

Pratt, L.A. et al., "Genetic Analyses of Bacterial Biofilm Formation," *Current Opinion in Microbiology*, 1999, vol. 2, pp. 598-603.

Qi, F. et al., "Purification of Mutacin III From Group III *Streptocuccus mutans*, UA787 and Genetic Analyses of Mutacin III Biosythesis Genes," *Applied and Environmental Microbiology*, Sep. 1999, vol. 65, No. 9, pp. 3880-3887.

Qi, F. et al., "The Group I Strain of *Streptococcus mutans*, UA140, Produces Both the Lantibiotic Mutacin I and a Nonantiobiotic Bacteriocin, Mutacin IV," *Applied and Environmental Microbiology*, Jan. 2001, vol. 67, No. 1, pp. 15-21.

Qiu, X-Q. et al., "An Engineered Multidomain Bactericidal Peptide as a Model for Targeted Antibiotics Against Specific Bacteria," *Nature Biotechnology*, Dec. 2003, vol. 21, No. 12, pp. 1480-1485.

Ruzheinikov, S.N. et al., "The 1.2 Å Structure of a Novel Quorum-Sensing Protein, *Bacillus subtilis* LuxS," *J. Mol. Biol.*, 2001, vol. 313, pp. 111-122.

Sal-Man, N. et al., "Preassembly of Membrane-Active Peptides is an Important Factor in Their Selectivity Toward Target Cells," *Biochemistry*, 2002, vol. 41, pp. 11921-11930.

Sawai, M.V. et al., "Impact of Single-Residue Mutations on the Structure and Function of Ovispirin/novispirin Antimicrobial Peptides," *Protein Engineering*, 2002, vol. 15, No. 3, pp. 225-232.

Schauder, S. et al., "The LuxS Family of Bacterial Autoinducers: Biosynthesis of a Novel Quorum-Sensing Signal Molecule," *Molecular Microbiology Biology*, 2001, vol. 41, No. 2, pp. 463-476.

Schröder, J-M., "Commentary: Epithelial Peptide Antibiotics," *Biochemical Pharmacology*, 1999, vol. 57, pp. 121-134.

Shai, Y., "Mechanism of the Binding, Insertion and Destabilization of Phospholipid Bilayer Membranes by α-Helical Antimicrobial and Cell Non-Selective Membrane-Lytic Peptides," *Biochimica et Biophysica Acta*, 1999, vol. 1462, pp. 55-70.

Shai, Y., "Mode of Action of Membrane Active Antimicrobial Peptides," *Biopolymers*, 2002, vol. 66, pp. 236-248.

Sharma, A.K. et al., "Transgenic Plants for the Production of Edible Vaccines and Antibodies for Immunotherapy," *Current Science*, Aug. 25, 1999, vol. 77, No. 4, pp. 524-529.

Shi, W. et al., "Rapid and Quantitative Detection of *Streptococcus mutans* with Species-Specific Monoclonal Antibodies," *Hybridoma*, 1998, vol. 17, No. 4, pp. 365-374.

Sperandio, V. et al., "Quorum Sensing Controls Expression on the Type III Secretion Gene Transcription and Protein Secretion in Enterohemorrhagic and Enteroptahogenic *Escherichia coli*," *PNAS*, Dec. 21, 1999, vol. 96, No. 26, pp. 15196-15201.

Stickler, D., "Biofilms," *Current Opinion in Microbiology*, 1999, vol. 2, pp. 270-275.

Stoodley, P. et al., "Biofilms as Complex Differentiated Communities," *Ann. Rev. Microbiol.*, 2002, vol. 56, pp. 187-209.

Surette, M.G. et al., "Quorum Sensing in *Escherichia coli* and *Salmonella typhimurium*," *Proc. Natl. Acad. Sci. USA*, Jun. 1998, vol. 95, pp. 7046-7050.

Surette, M.G. et al., "Quorum Sensing in *Escherichia coli, Salmonella typhimuruium*, and *Vibrio harveyi*: A New Family of Genes Responsible for Autoinducing Production," *Proc. Natl. Acad. Sci. USA*, Feb. 1999, vol. 96, pp. 1639-1644.

Tamamura, H. et al., "Synthesis of Protegrin-Related Peptides and Their Antibacterial and Anti-Human Immunodeficiency Virus Activity," *Chem. Pharm. Bull.*, 1995, vol. 43, No. 5, pp. 853-858.

Tossi, A. et al., "Amphipathic, α-Helical Antimicrobial Peptides," *Biopolymers*, 2000, vol. 55, pp. 4-30.

Travis, S.M. et al., "Bactericidal Activity of Mammalian Cathelicidin-Dervied Peptides," *Infection and Immunity*, May 2000, vol. 68, No. 5, pp. 2748-2755.

U.S. Appl. No. 09/378,577, filed Aug. 20, 1999, for Wenyuan Shi et al.

U.S. Appl. No. 11/851,372, filed Sep. 6, 2006, for Randal H. Eckert et al.

U.S. Appl. No. 12/014,634, filed Jan. 15, 2008, for Jian He et al.

U.S. Appl. No. 12/065,033, filed Feb. 27, 2008, for Daniel K. Yarbrough et al.

U.S. Appl. No. 12/066,822, filed Mar. 13, 2008, for Daniel K. Yarbrough et al.

Van Raamsdonk, M. et al., "Effect of Monoclonal Antibodies on the Colonization of Rats by *Streptococcus sobrinus*," *Caries Research*, 1993, vol. 27, pp. 31-37.

Van Raamsdonk, M. et al., "Effect of Antibodies on Chemiluminescence and on Killing of *Streptococcus sobrinus* by Polymorphonuclear Leukocytes," *Oral Microbiology and Immunology*, 1996, vol. 11, No. 4, pp. 254-258.

Vogel, H.J. et al., "Towards a Structure-Function Analysis of Bovine Lactoferricin and Related Tryptophan- and Arginine-Containing Peptides," *Biochem Cell Biol*, 2002, vol. 80, pp. 49-63.

Vuong, C. et al., "Impact of the *agr* Quorum-Sensing System on Adherence to Polystyrene in *Staphylococcus aureus*," *The Journal of Infectious Diseases*, 2000, vol. 182, pp. 1688-1693.

Wei, S-Y. et al., "Solution Structure of a Novel Tryptophan-Rich Peptide with Bidirectional Antimicrobial Activity," *Journal of Bacteriology*, Jan. 2006, vol. 188, No. 1, pp. 328-334.

Wen, Z.T. et al., "Functional Genomics Approach to Identifying Genes Required to Biofilm Development by *Streptococcus mutans*," *Applied and Environmental Microbiology*, Mar. 2002, vol. 68, No. 3, pp. 1196-1203.

Wessolowski, A. et al., "Antimicrobial Activity of Arginine- and Trytophan-Rich Hexapeptides: The Effects of Aromatic Clusters, D-Amino Acid Substitution and Cyclization," *J. Pept. Res.*, 2004, vol. 64, pp. 159-169.

Wimmer, R. et al., "Versatile Interactions of the Antimicrobial Peptide Novispirin with Detergents and Lipids," *Biochemistry*, 2006, vol. 45, No. 2, pp. 481-497.

Wolinsky, L.E. et al., "The Inhibiting Effect of Aqueous *Azradirachta indica* (Neem) Extract Upon Bacterial Properties Influencing in vitro Plaque Formation," *J. Dent. Res.*, Feb. 1996, vol. 75, No. 2, pp. 816-822.

Yasin, B. et al., "Susceptibility of *Chlamydia trachomatis* serovars L2, D, and E to G-10 novispirin," Database Biosis Biosciences Information Service: Philadelphia, PA, 2001, 2 pages.

Yoshida, A. et al., "Molecular Analysis of the *Streptococcus mutans* Genes Involved in Biofilm Formation," *Abstracts of the General Meeting of the American Society for Microbiology*, May 2001, vol. 101, Abstract No. D. 242, pp. 326-327.

Yoshida, A. et al., "Role of the *Streptococcus mutan luxS* Gene in Biofilm Formation," *Abstracts of the General Meeting of the American Society for Microbiology*, May 2002, vol. 102, Abstract No. D. 27, p. 161.

Jun, Z., "Some bioactive substances from plants of West China," *Pure & Appl. Chem.*, 1989, vol. 61, No. 3, pp. 457-460.

Ma, J.C.N. et al., "Structure Characterization of Haemostatic Diosgenin Glycosides from *Paris polyohylia*," *Phytochemistry*, 1985, vol. 24, No. 7, pp. 1561-1565.

Namba, T. et al., "Chronotropic Effect of the Methanolic Extracts of the Plants of the *Paris* Species and Steroidal Glycosides Isolated from *P. vietnamensis* on Spontaneous Beating of Myocardial Cells," *Planta medica*, 1989, vol. 55, pp. 501-505.

\* cited by examiner

COMPOSITIONS USEFUL FOR THE TREATMENT OF MICROBIAL INFECTIONS

FIELD OF THE INVENTION

The invention relates generally to treatment of microorganisms, and more specifically to compositions isolated from herbs useful in treating microbial infections.

BACKGROUND INFORMATION

Modern medical science is constantly searching for new and more powerful agents to prevent, treat or retard bacterial and viral infections and cure the diseases they cause. Bacterial and viral infections of humans and domestic animals cost billions of dollars annually. Vast sums of money are spent each year by pharmaceutical companies to identify, characterize, and produce new antibiotics and antivirals to combat the emerging drug resistant strains which have become a serious problem. Reliable prophylactic treatments for disease prevention are also of major interest.

Specifically periodontal disease and dental caries are of major public health and economic interest worldwide. It is now widely recognized that both of these oral diseases are caused by bacteria which grow in masses on the teeth and in the gingival and subgingival areas. A commonly used descriptive term for these bacterial masses is "dental plaque". In the case of periodontal disease, it has been reported that dental plaque bacteria, growing in the area where the teeth and gingival tissues meet, cause an inflammation of the gingiva called "gingivitis". This is characterized by swollen, edematous gingiva ("gums") which are reddened and bleed easily. If plaque removal is inadequate, gingivitis may progress to "periodontitis" or periodontal disease in some individuals. Periodontitis generally is characterized by a chronic inflammation of the tissues around the teeth, which leads to a resorption of supporting bone. Periodontal disease is the leading cause of tooth loss among adults.

Dental caries (cavities) are also caused by bacteria, with *mutans Streptococcus* being the principal etiologic agent. Dental caries is a prevalent and costly disease throughout the world. The latest report by NIH indicated that 49% of 12-year-old and 79% of 17-year-old children in the USA have dental caries. A very high percentage of the elderly also have tooth decay manifest as root caries.

Tooth decay is mainly caused by a group of cariogenic Gram-positive bacteria such as *Streptococcus mutans*. Given a suitable carbohydrate nutrient (simple dimer sugars like sucrose), these bacteria produce insoluble glucans and acids in dental plaque. The glucans produced by *S. mutans* are very sticky, enabling it to adhere to the tooth's surface while the acids attack the tooth's mineral structure causing demineralization that may lead to cavitation.

The prevention of dental plaque or the removal thereof has long been the focus of development, with the ultimate goal of inhibiting both caries and periodontal diseases. While the formation of dental plaque can be inhibited to a certain extent by brushing the teeth at frequent intervals, brushing alone is not sufficient to effectively prevent the formation of dental plaque or remove substantially all of the dental plaque that has formed on the teeth. Since brushing alone is often not sufficient to prevent dental caries or periodontal disease due to the nature of the pathogenic plaque bacteria, chemical methods using anti-bacterials such as chlorhexidine, benzalkonium chloride, and cetylpyridinium chloride have been proposed.

There is a need in the art to provide compositions and methods useful for treating or preventing microbial conditions, e.g., oral or mucosal surface microbial conditions.

SUMMARY OF THE INVENTION

The present invention is based on the discovery that certain chemical compounds isolated from Chinese medicinal herbs are useful as anti-microbial agents, e.g., anti-bacterial agents, anti-fungal agents, agents capable of disrupting bacterial quorum sensing, and the like. In particular, the present invention provides compositions and methods useful for inhibiting the activity of microorganisms and/or treating microbial infections such as, for example, oral or mucosal surface microbial infections.

In one embodiment, the present invention provides a composition comprising at least two compounds selected from the group consisting of kurarinone, berberine, dioscin, perillaldehyde, α-linolenic acid, and polyphyllin D.

In another embodiment, the present invention provides a composition comprising perillaldehyde and at least one compound selected from the group consisting of kurarinone, berberine, dioscin, α-linolenic acid, and polyphyllin D.

In yet another embodiment, the present invention provides a composition comprising polyphyllin D and at least one compound selected from the group consisting of kurarinone, berberine, α-linolenic acid, and perillaldehyde.

In still another embodiment, the present invention provides a composition comprising dioscin and at least one compound selected from the group consisting of kurarinone, berberine, α-linolenic acid, and perillaldehyde.

In another embodiment, the present invention provides a composition comprising kurarinone, berberine, dioscin, and α-linolenic acid.

In another embodiment, the present invention provides a composition comprising kurarinone, berberine, α-linolenic acid, and polyphyllin D.

In yet another embodiment, the present invention provides a pharmaceutical composition comprising an active component and a pharmaceutically acceptable carrier, wherein the active component consists at least one compound selected from the group consisting of kurarinone, berberine, dioscin, perillaldehyde, α-linolenic acid, and polyphyllin D.

In yet another embodiment, the present invention provides a pharmaceutical composition comprising an active component and a pharmaceutically acceptable carrier, wherein the active component comprises perillaldehyde and at least one compound selected from the group consisting of kurarinone, berberine, dioscin, perillaldehyde, α-linolenic acid, and polyphyllin D.

In still another embodiment, the present invention provides a formulation suitable for topical administration comprising the composition of the present invention.

In yet another embodiment, the present invention provides an oral hygiene product comprising the composition of the present invention.

In yet another embodiment, the present invention provides a food additive composition comprising the composition of the present invention.

In another embodiment, the present invention provides a method of inhibiting the activity of a microorganism. The method comprises contacting the microorganism with a composition of at least one compound selected from the group consisting of kurarinone, berberine, dioscin, perillaldehyde, α-linolenic acid, and polyphyllin D.

In yet another embodiment, the present invention provides a method of treating or preventing a microbial infection. The method comprises administering to a subject in need of such treatment a composition comprising at least one compound selected from the group consisting of kurarinone, berberine, dioscin, perillaldehyde, α-linolenic acid, and polyphyllin D.

In yet another embodiment, the present invention provides a method of preventing a microbial infection. The method comprises contacting a composition to an area susceptible to a microorganism causing the microbial infection, wherein the composition comprises at least one compound selected from the group consisting of kurarinone, berberine, dioscin, perillaldehyde, α-linolenic acid, and polyphyllin D.

DETAILED DESCRIPTION OF THE INVENTION

The present invention is based on the discovery that certain chemical compounds isolated from Chinese medicinal herbs are useful as anti-microbial agents, e.g., anti-bacterial agents, anti-fungal agents, agents capable of disrupting bacterial quorum sensing, and the like. Accordingly, the present invention provides compositions and methods useful for inhibiting the activity of microorganisms and/or treating microbial infections such as, for example, oral or mucosal surface microbial infections.

In particular, six compounds from four medicinal Chinese herbs have been isolated and found to have anti-microbial activity. Specifically, kurarinone has been isolated from the herb *Sophora flavescens*; berberine has been isolated from the herb *Coptis chinensis*; α-linolenic acid and perillaldehyde have been isolated from the herb *Perilla frutescens*; and polyphyllin D and dioscin have been isolated from the herb *Paris polyphylla*.

These six compounds have the following structures:

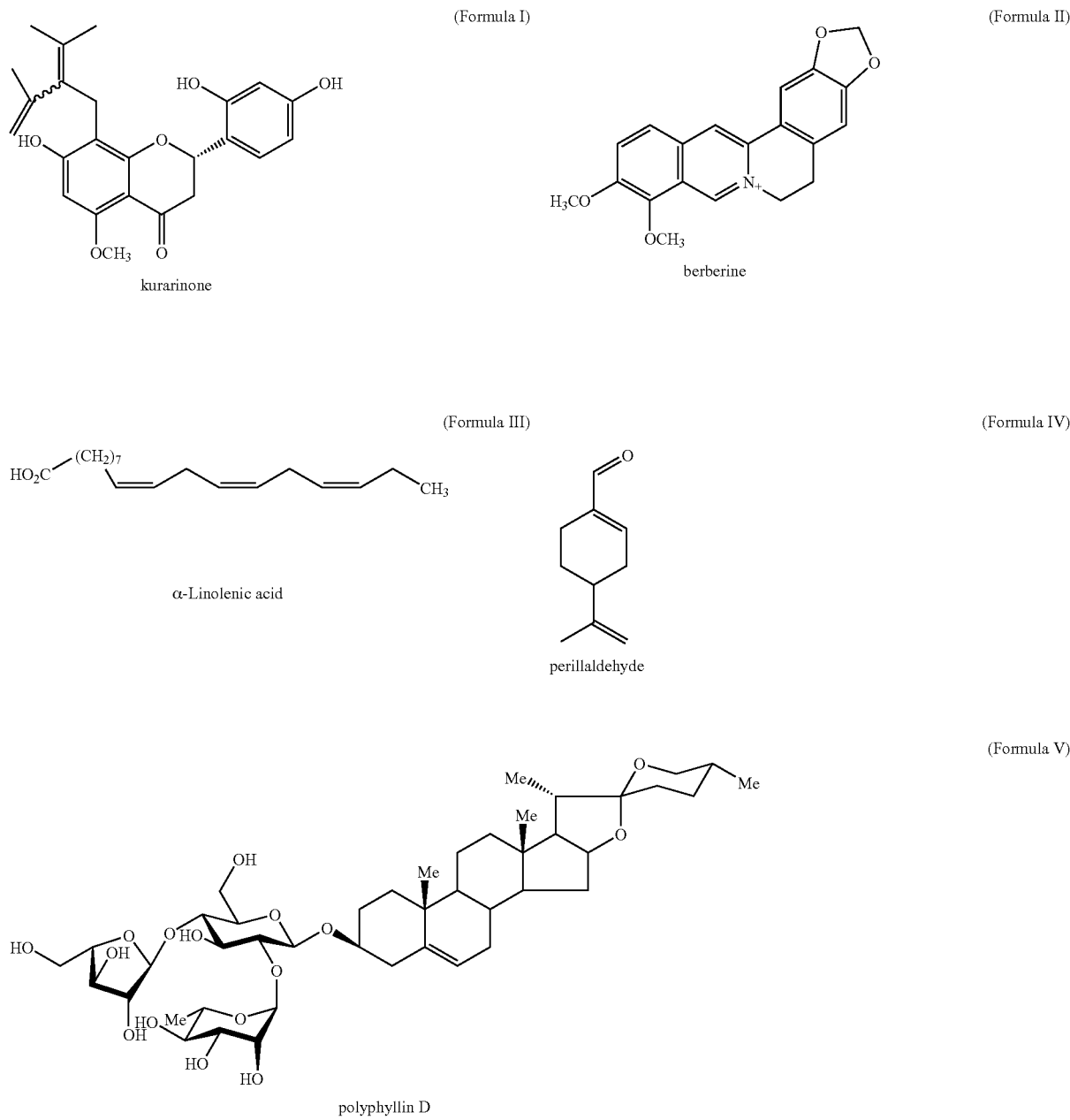

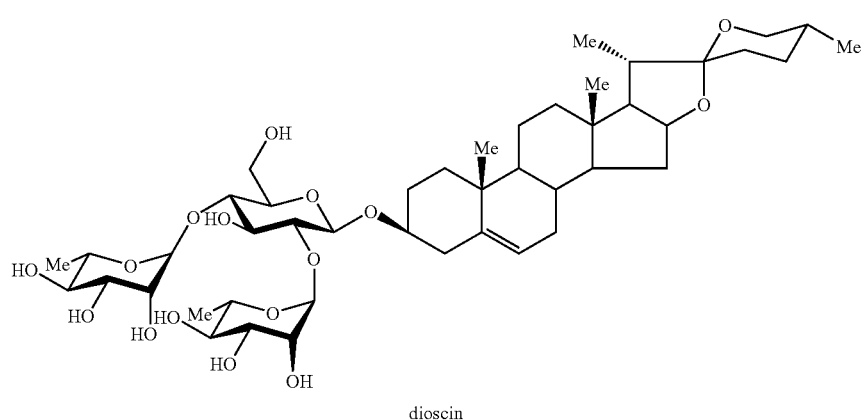

dioscin (Formula VI)

According to one feature of the present invention, it provides compositions useful for treating microorganisms, e.g., inhibiting the activity of microorganisms. The composition of the present invention includes at least one, two, three or four compounds of a group of compounds isolated from herbs, e.g., Chinese medicinal herbs of *Sophora flavescens, Coptis chinensis, Perilla frutescens*, and *Paris polyphylla*.

In one embodiment, the composition of the present invention includes at least one, two, three, or four compounds of a group of compounds comprised of kurarinone, berberine, dioscin, perillaldehyde, α-linolenic acid, and polyphyllin D. According to the present invention, the compound of kurarinone, berberine, α-linolenic acid, perillaldehyde, polyphyllin D, or dioscin includes any naturally existing or chemically synthesized original compound, e.g., compound having the chemical structure as shown in Formula I (ACS No. 34981-26-5), II (ACS No. 2086-83-1), III (ACS No. 463-40-1), IV (ACS No. 2111-75-3), V (ACS No. 50773-41-6), or VI (ACS No. 19057-60-4), respectively and any derivatives thereof, excluding any naturally existing herbs containing one or more original compounds such as *Sophora flavescens, Coptis chinensis, Perilla frutescens*, and *Paris polyphylla*. For example, the original compound of kurarinone, berberine, α-linolenic acid, perillaldehyde, polyphyllin D and dioscin is 1) 2-(2,4-dihydroxyphenyl)-2,3-dihydro-7-hydroxy-5-methoxy-8-[5-methyl-2-(1-methylethenyl)-4-hexenyl]-4H-1-benzopyran-4-one, 2) 5,6-dihydro-9,10-dimethoxy-benzo[g]-1,3-benzodioxolo[5,6 a]quinolizinium, 3) (9Z,12Z,15Z)-9,12,15-octadecatrienoic acid, 4) 4-(1-methylethenyl)-1-cyclohexene-1-carboxaldehyde, 5) (3β,25R)-spirost-5-en-3-yl O-α-L-arabinofuranosyl-(1→4)-O-[6-deoxy-α-L-mannopyranosyl-(1→2)]-β-D-glucopyranoside, and 6) (3β,25R)-spirost-5-en-3-yl O-6-deoxy-α-L-mannopyranosyl-(1→2)-O-[6-deoxy-α-L-mannopyranosyl-(1→4)]-β-D-glucopyranoside, respectively.

Derivatives of these original compounds include any compounds obtainable via modifying the original compounds of kurarinone, berberine, α-linolenic acid, perillaldehyde, polyphyllin D, or dioscin or any compound containing one or more key structural features of these original compounds, provided that these compounds still maintain the same or different level of anti-microbial activity contained within the original compounds. In addition, the compound of kurarinone, berberine, α-linolenic acid, perillaldehyde, polyphyllin D, or dioscin can be in any form, e.g., salt, including without any limitation, hydrochloride, bisulfate, sulfate, etc.

In another embodiment, the composition of the present invention includes a compound capable of enhancing the anti-microbial activity of another compound and at least one, two, or three compounds having anti-microbial activity. For example, the composition of the present invention can include perillaldehyde and at least one, two, or three compounds of a group of compounds comprised of kurarinone, berberine, dioscin, α-linolenic acid, and polyphyllin D.

In yet another embodiment, the composition of the present invention includes a compound with anti-fungal activity and at least one compound with anti-bacterial activity. For example, the composition of the present invention can include polyphyllin D and at least one compound of a group of compounds comprised of kurarinone, berberine, α-linolenic acid, and perillaldehyde. Alternatively the composition of the present invention can include dioscin and at least one compound of a group of compounds comprised of kurarinone, berberine, α-linolenic acid, and perillaldehyde.

In still another embodiment, the composition of the present invention includes at least kurarinone, berberine, dioscin, and α-linolenic acid, or kurarinone, berberine, α-linolenic acid and polyphyllin D.

According to another feature of the present invention, the composition of the present invention is a pharmaceutical composition, e.g., useful for inhibiting the activity of microorganisms or treating microbial infection. The pharmaceutical composition of the present invention includes a pharmaceutically acceptable carrier and one or more active components derived from compounds isolated from herbs e.g., Chinese medicinal herbs of *Sophora flavescens, Coptis chinensis, Perilla frutescens*, and *Paris polyphylla*.

In one embodiment, the pharmaceutical composition of the present invention includes a pharmaceutically acceptable carrier and an active component including at least one, two, three, or four compounds of a group of compounds comprised of kurarinone, berberine, dioscin, perillaldehyde, α-linolenic acid, and polyphyllin D.

In another embodiment, the pharmaceutical composition of the present invention includes a pharmaceutically acceptable carrier and an active component including compounds derived from herbs, but not from other sources. For example, the pharmaceutical composition of the present invention can include a pharmaceutically acceptable carrier and an active component derived solely from kurarinone, berberine, dioscin, perillaldehyde, α-linolenic acid, and/or polyphyllin D, e.g., an active component including at least one, two, three, or four compounds of a group of compounds comprised of kurarinone, berberine, dioscin, perillaldehyde, α-linolenic acid, and polyphyllin D.

In yet another embodiment, the pharmaceutical composition of the present invention includes a pharmaceutically acceptable carrier and an active component including a compound having anti-fungal activity and a compound having anti-bacterial activity. For example, the pharmaceutical composition of the present invention includes a pharmaceutically acceptable carrier and an active component including polyphyllin D or dioscin and at least one compound selected from the group of kurarinone, berberine, perillaldehyde, and α-linolenic acid.

In still another embodiment, the pharmaceutical composition of the present invention includes a pharmaceutically acceptable carrier and an active component including a compound capable of enhancing the anti-microbial activity of other compounds and at least one compound with anti-microbial activity. For example, the pharmaceutical composition of the present invention can include a pharmaceutically acceptable carrier and an active component including perillaldehyde and at least one, two, three or four compounds selected from the group of polyphyllin D, dioscin, kurarinone, berberine, and α-linolenic acid.

The composition or pharmaceutical composition of the present invention can also be provided as a formulation suitable for topical administration, oral hygiene product, or food additive. In addition, the composition of the present invention can also include one or more other non-active ingredients, e.g., ingredients that do not interfere with the function of the active ingredients. For example, the compositions of the present invention can additionally contain any of a variety of added components, such as, for example, preservatives, solubilizers, stabilizers, wetting agents, emulsifiers, sweeteners, colorants, flavorings, buffers, coating agents, antioxidants, diluents, and the like. In addition, the composition of the present invention can include a suitable carrier or be combined with other therapeutic agents.

A suitable carrier can be an aqueous carrier including any safe and effective materials for use in the compositions of the present invention. In one embodiment, an aqueous carrier is used for the compositions of the present invention in oral formations and includes, without limitation, thickening materials, humectants, water, buffering agents, abrasive polishing materials, surfactants, titanium dioxide, flavor system, sweetening agents, coloring agents, and mixtures thereof.

A suitable carrier can also be a pharmaceutically acceptable carrier that is well known to those in the art, e.g., large, slowly metabolized macromolecules, polysaccharides, polylactic acids, polyglycolic acids, polymeric amino acids, amino acid copolymers, and inactive virus particles. A pharmaceutically acceptable carrier can be a solid carrier or a liquid carrier. Examples of solid carriers include lactose, sucrose, talc, gelatin, agar, pectin, acacia, magnesium stearate, stearic acid, or lower alkyl ethers of cellulose. Examples of liquid carriers include syrup, peanut oil, olive oil, phospholipids, fatty acids, fatty acid amines, polyoxyethylene or water. The carrier or diluent may include any sustained release material known in the art, such as glyceryl monostearate or distearate, alone or mixed with a wax.

Pharmaceutically acceptable salts can also be used in the composition, for example, mineral salts such as sodium or stannous fluorides, or sulfates, as well as the salts of organic acids such as acetates, proprionates, carbonates, malonates, or benzoates. The composition can also contain liquids, e.g., water, saline, glycerol, and ethanol, as well as substances, e.g., wetting agents, emulsifying agents, or pH buffering agents.

If a solid carrier is used for oral administration, the preparation may be tabletted or placed in a hard gelatin capsule in powder or pellet form. The amount of solid carrier will vary widely, but will usually be from about 25 mg to about 1 gm. If a liquid carrier is used, the preparation may be in the form of a syrup, emulsion, soft gelatin capsule, sterile injectable liquid such as an aqueous or non-aqueous liquid suspension or solution, and the like.

Tablets are prepared by mixing compositions of the present invention with pharmaceutically inert, inorganic or organic carrier, diluents, and/or excipients. Examples of such excipients which can be used for the preparation of tablets include lactose, maize starch or derivatives thereof, talc, stearic acid or salts thereof. Examples of suitable excipients for gelatin capsules include vegetable oils, waxes, fats, semisolid, and liquid polyols. The lipid analogs can also be made in microencapsulated form.

For nasal administration, the preparation may contain compositions of the invention dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

The present invention embraces the use of pharmaceutical compositions for containing pharmaceutically acceptable sterile aqueous or non-aqueous liquids, dispersions, suspensions or emulsions as well as sterile powders for reconstitution into sterile injectable solutions or dispersions just prior to use parenteral injection. Pharmaceutical formulations containing compounds of the present invention can be prepared by conventional techniques, e.g., as described in *Remington's Pharmaceutical Sciences*, 1985.

The compositions of the present invention usually have an anti-microbial effect, e.g., anti-$G^+$ bacteria activity, anti-$G^-$ bacteria activity, anti-fungus activity or effect on bacterial quorum sensing. Methods or assays for testing the anti-microbial activity of a composition are readily available to one skilled in the art. For example, compositions of the present invention can be incubated with a bacterial or fungous culture, and the bacterial or fungous growth can be subsequently examined with a plate reader. Compositions of the present invention can also be examined for their effect on bacterial quorum sensing using either an acyl-homoserine lactone quorum sensing reporter system or a luxS quorum sensing reporter system.

According to another feature of the present invention, the compositions of the present invention can be used to treat or prevent microbial growth or infection, e.g., inhibit the activity of bacteria or fungi in vivo or in vitro. For example, the compositions of the present invention can be used to inhibit microbial flora, especially microbial flora associated with dental structures such as tooth surface or subsurface or caries, e.g., microbial flora associated with demineralized areas, white spots, pits, and fissures or microbial flora associated with mucosal surfaces.

In one embodiment, the compositions of the present invention can be used to inhibit microorganisms including without limitation *S. mutans, S. sobrinus, S. aureus, L. acidophilus, L. casei, L. plantarum, A. naeslundii, A. viscosus, Actinobacillus actinomycetemcomitans, Porphyromonas gingivalis, Enterococci, Fusobacterium nucleatum, Treponema denticola, Bacteroides forsythus, Candidas albicans, C. glabrata, C. guilliemondii, C. kefyr, C. krusei, C. stellatoidea* and *C. tropicalis*.

In another embodiment, the composition of the present invention can be used to inhibit the activity of cariogenic bacteria, including without limitation, *Mutans streptococci, lactobacilli* and *actinomyces*, e.g., *S. mutans, S. sobrinus, A. viscosus, A. naeslundii, L. acidophilus, L. casei,* and *L. plantarum*. In yet another embodiment, the composition of the present invention can be used to inhibit the activity of fungi, e.g., *Candidas albicans, C. glabrata, C. guilliemondii, C. kefyr, C. krusei, C. stellatoidea* and *C. tropicalis*.

In still another embodiment, the composition of the present invention can be used to inhibit the activity of drug resistant microorganisms. According to the present invention, a drug resistant microorganism is a microorganism that does not substantially respond to a routinely used antibiotic or respond to an extent below the average response induced by a routinely used antibiotic. For example, the composition of the present invention can be used to treat methicillin resistant *S. aureus*, Vancomycin resistant *Enterococci*, or clinically isolated drug resistant *C. albicans*. In still yet another embodiment, the composition of the present invention containing at least kurarinone can be used to treat methicillin resistant *S. aureus* and Vancomycin resistant *Enterococci* while the composition of the present invention containing at least polyphyllin D can be used to treat drug-resistant *C. albicans*.

According to another feature of the present invention, it provides a method of inhibiting the activity of microorganisms from one or more species or preventing a microbial infection by contacting one or more compositions of the present invention to the microorganisms. The present invention also provides a method for treating or preventing a microbial infection by administering to a subject in need of such treatment an effective amount of one or more compositions of the present invention. The subject in need of such treatment can be any suitable subject, e.g., a human or an animal including a domestic animal such as a horse, dog, or cat. The microbial infection can be any infection caused by one or more microorganisms of one or more species including without limitation microbial infections associated with drug resistant microorganisms, e.g., *S. aureus, Enterococci,* and *C. albicans* and/or multi-species biofilms.

In generally, an effective amount of the compositions to be administered can be determined on a case-by-case basis. Factors to be considered usually include age, body weight, stage of the condition, other disease conditions, duration of the treatment, and the response to the initial treatment. The term "effective amount" as applied to the compositions of the present invention is an amount that will prevent or inhibit the disorders associated with microbial infections noted above. The selected dosage will vary depending on the activity of the selected compound, the route of administration, the severity of the condition being treated, and the condition and prior medical history of the patient being treated. If desired, the effective daily dose may be divided into multiple doses for purposes of administration, for example, two to four doses per day.

Typically, the compositions are prepared as a topical or an injectable, either as a liquid solution or suspension. However, solid forms suitable for solution in, or suspension in, liquid vehicles prior to injection can also be prepared. The composition can also be formulated into tablets, e.g., an enteric-coated tablet, capsules, e.g., gel capsules, emulsions, inhaled liquid or solid particles, microencapsulated particles, e.g., as a spray, or transdermal patches according to known methods in the art.

The compositions of the present invention may be administered in any way which is medically acceptable which may depend on the condition or injury being treated. Possible administration routes include injections, by parenteral routes such as intravascular, intravenous, intraepidural or others, as well as oral, nasal, ophthalmic, rectal, vaginal, topical, or pulmonary, e.g., by inhalation. The compositions may also be directly applied to tissue surfaces. Sustained release, pH dependent release, or other specific chemical or environmental condition mediated release administration is also specifically included in the invention, by such means as depot injections or erodible implants.

In one embodiment, the composition of the present invention can be used to treat or prevent microbial infections associated with epithelial tissues or skins, e.g., wounds, burns, acne, fungus infection on skins such as foot, and other skin conditions or with opportunistic organisms, e.g., opportunistic organisms superinfect a site.

In another embodiment, the composition of the present invention can be used to treat or prevent microbial infections on mucosal surfaces, e.g., mouth, vagina, gastrointestinal (GI) tract, esophageal tract, and respiratory tract. For example, the composition of the present invention can be used to treat or prevent *Streptococcus* throat, *Streptococcus pneumoniae*, nontypeable *Haemophilius influenza*, or *Moraxella cararrhalis* infection commonly found in acute otitis media (AOM) and otitis media effusion (OME) as complications of upper respiratory infections in young children.

In another example, the composition of the present invention can be used to treat or prevent GI tract infections including without limitation duodenal or gastric ulcers associated with *Helicobacter pylori* (*H. pylori*) bacteria infection, *campylobacter* bacterial infection, diarrhea primarily associated with *Campylobacter jejuni*, cholera caused by *Vibrio cholerae* serogroups, salmonellosis caused by bacteria *salmonella* such as *S. Typhimurium* and *S. Enteritidis*, shigellosis caused by bacteria *Shigella*, e.g., *Shigella dysenteriae* and traveler's diarrhea caused by enterotoxigenic *Escherichia coli* (ETEC) and *Clostridium difficile* infection.

In yet another example, the composition of the present invention can be used to treat yeast or *Candida* infections (Candidiasis) typically occur either orally (Oropharyngeal *Candida* or OPC) or vaginally (Vulvovaginal *Candida* or VVC).

According to another embodiment of the present invention, the compositions of the present invention are used to treat or prevent cariogenic organism infections, e.g., *S. mutans* infection associated with dental caries, including without limitation tooth surface or subsurface associated with demineralized areas, white spots, pits, and fissures. One or more compositions of the present invention can be prepared as additives to food, oral hygiene product, or any products having direct contact to an oral environment, especially an oral environment susceptible to dental caries or periodontal diseases. For instance, to treat or prevent dental caries or periodontal diseases compositions of the present invention can be formulated into a baby formula, mouthwash, lozenges, gel, varnish, toothpaste, toothpicks, tooth brushes, or other tooth cleansing devices, localized delivery devices such as sustained release polymers or microcapsules, oral irrigation solutions of any kind whether mechanically delivered or as oral rinses, pacifiers, and any food including, without limitation, chewing gums, candies, drinks, breads, cookies, and milk.

The invention will now be described in greater detail by reference to the following non-limiting examples.

Example 1

Isolation of Kurarinone from *Sophora flavescens*

*Sophora flavescens* is one of the common medicinal herbs used by Traditional Chinese Medicine (TCM) doctors. In traditional practice, it has been used to alleviate heat, toxin, constipation, and masses, and to disperse painful swelling in the throat, mouth, and gums. Recently, in vitro pharmacological studies indicated that the extract of *Sophora flavescens* constitutes a variety of biomedical activities for inflammation, cancer, and cardiovascular disorders.

The following steps were applied to purify the active compound(s) for structure analysis: 1) the crude extract of *Sophora flavescens* was suspended in 10% methanol; 2) the aqueous solution was extracted with ethyl acetate; 3) the organic layers were concentrated at 40° C. under reduced pressure; 4) the extract was then chromatographed over silica gel (500 grams), 100-200 mesh (Selecto, George), eluted with gradient hexane:ethyl acetate; 5) the most active fractions were pooled and then further purified by HPLC (Waters, 600E system controller and Waters996 Photodiode Array Detector, Millord, Mass.). Waters SymmetryPrep C-18 column (4.6×250 mm). Through bio-assay oriented chemical analysis, it was found that the major anti-bacterial compound isolated from this herb is kurarinone.

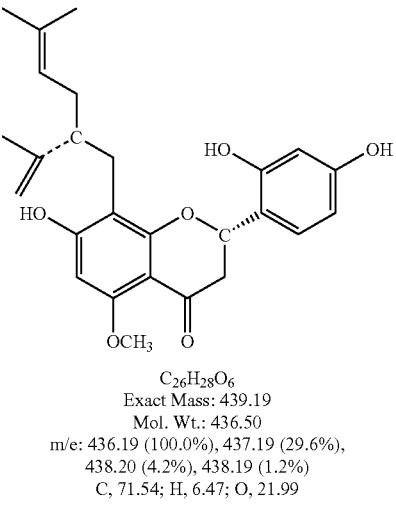

$C_{26}H_{28}O_6$
Exact Mass: 439.19
Mol. Wt.: 436.50
m/e: 436.19 (100.0%), 437.19 (29.6%), 438.20 (4.2%), 438.19 (1.2%)
C, 71.54; H, 6.47; O, 21.99

This study of purified kurarinone demonstrated that kurarinone has a strong anti-bacterial activity, for example, its MIC for *S. mutans* is 4 μg/ml. The compound also has a bactericidal effect. In addition, the antimicrobial activity of this compound is insensitive to the following environmental changes: pH (4.8-7.4); salt composition (Na, K, Ca); salt concentrations; oxygen levels (anaerobic and aerobic); and temperature (120° C.). Finally, both methicillin resistant *Staphylococcus aureus* and Vancomycin resistant *Enterococci* are sensitive to this compound.

Example 2

Isolation of α-Linolenic Acid and Perillaldehyde from *Perillae folium*(Suye, SY)

*Perillae folium* is a flower commonly seen in Japan and China. It is believed to have power in clear fish and crab poisoning and relieve cough. It is used with other herbs in herbal bath for its oil. It also counteracts fatigue and acts as a preventive against dysentery.

*Perilla* was selected for two types of bioactivity. The first is a weak antibacterial activity identified through conventional antibacterial assay. The second is its ability to enhance other antibacterial activities through some kind of synergistic effect. When the crude extract was mixed with antibiotics in the bioassay, it could enhance the activity of other antibiotics at a concentration at least 10 times lower than its MIC.

Bioassay-based phytochemical analyses were conducted to isolate and characterize the active components from SY. The active components were purified from the crude SY extract by hexane extraction and chromatograph through silica gel. The most active fractions were pooled and then further purified by HPLC. Two active compounds were isolated from this herb. Structure analysis demonstrated that one is α-linolenic acid and the other is perillaldehyde.

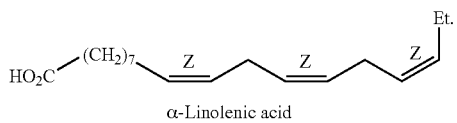

α-Linolenic acid

Our study of linolenic acid demonstrated:
1) Linolenic acid has a strong growth inhibitory effect against *S. mutans*. Its MIC for *S. mutans* is 10 μg/ml.
2) Linolenic acid is known as one of the major components of perilla oil.

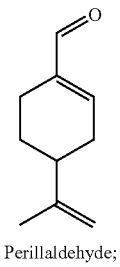

Perillaldehyde;

Our study on perillaldehyde demonstrated:
1). The compound has a weak anti-bacterial activity (MIC for *S. mutans:* 10 mg/ml).
2). The compound has the ability to enhance activity of other antibiotics in a dose-dependent manner.

Example 3

Isolation of Polyphyllin D and Dioscin from *Paris polyphylla* (QY)

Topical application of *Paris polyphylla* has been well documented in TCM practice. In a preliminary screening, a strong anti-fungal activity was identified. Two active compounds, polyphyllin D and diosocin, were isolated from this herb. For the purpose of structure analysis, purity is the primary concern in this study. Due to this concern, the yield of polyphyllin is low. Clearly, a simple and economic protocol is required for the production of both refined extract and the compound with a defined purity.

The first step of the purification is ethyl acetate extraction. The crude extract of QY was directly dissolved in ethyl acetate with sonication. The extract (QYEA) was concentrated under reduced pressure in a vacuum rotavapor. The yield of this step is around 0.5%. The recovery rate of total bioactivity is around 40%.

The QYEA (20 grams) was then chromatographed over silica gel (500 grams), 100-200 mesh (Selecto, George), eluted with gradient hexane:ethyl acetate:methanol (from 100:100:10 to 100:100:50). The yield of this step is around 10%. The recovery rate of total bioactivity is around 45%. The extract is labeled as QYEA-Si.

The active fraction was then further purified by HPLC (Waters, 600E system controller and Waters996 Photodiode Array Detector, Millord, Mass.). Waters SymmetryPrep C-18 column (4.6×250 mm) and the following gradient were used for this purpose.

| Time (minutes) | Flow rate (ml/minute) | Acetonitrile % | Water % |
|---|---|---|---|
| 1 |  | 2.00 | 10 | 90 |
| 2 | 10 | 2.00 | 45 | 55 |
| 3 | 35 | 2.00 | 65 | 45 |
| 4 | 37 | 2.00 | 10 | 90 |
| 5 | 45 | 2.00 | 10 | 90 |

Bioassays were conducted to further characterize these two compounds.

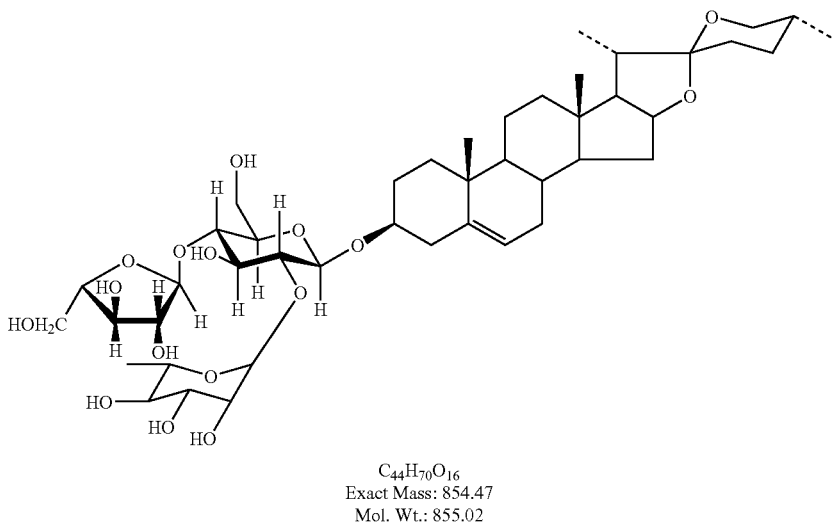

$C_{44}H_{70}O_{16}$
Exact Mass: 854.47
Mol. Wt.: 855.02

Studies of polyphyllin D indicated:
1. Polyphyllin D has a strong anti-fungal activity. Its MIC for *C. albicans* is around 2 μg/ml.
2. Polyphyllin D has a fungicidal effect.
3. Clinical isolated drug-resistant *C. albicans* are still sensitive to the Polyphyllin treatment.

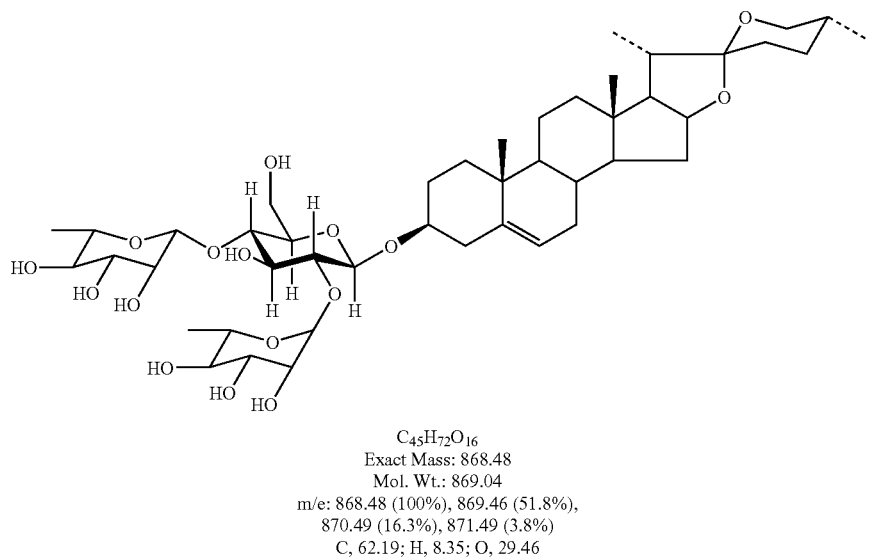

$C_{45}H_{72}O_{16}$
Exact Mass: 868.48
Mol. Wt.: 869.04
m/e: 868.48 (100%), 869.46 (51.8%),
870.49 (16.3%), 871.49 (3.8%)
C, 62.19; H, 8.35; O, 29.46

Studies of dioscin indicated:
1. Dioscin has a strong anti-fungal activity. Its MIC for *C. albicans* is around 4 μg/ml.
2. Dioscin has a fungicidal effect.
3. Clinical isolated drug-resistant *C. albicans* are still sensitive to the dioscin treatment.

Although the invention has been described with reference to the above example, it will be understood that modifications and variations are encompassed within the spirit and scope of the invention. Accordingly, the invention is limited only by the following claims.

What is claimed is:

1. A method of inhibiting the activity of a yeast or fungal microorganism, said method comprising contacting the yeast or fungal microorganism with a composition comprising polyphyllin D as an active ingredient, in an amount sufficient to inhibit the activity of said yeast, or fungal microorganism.

2. The method of claim 1, wherein the microorganism is an oral pathogenic microorganism.

3. The method of claim 1, wherein the microorganism causes dental caries or periodontal disease.

4. The method of claim 1, wherein the microorganism is on a mucosal surface.

5. The method of claim 1, wherein the microorganism is associated with a tooth structure.

6. The method of claim 1, wherein the microorganism is associated with an infection in an epithelial tissue.

7. The method of claim 1, wherein the microorganism is a drug resistant microorganism.

8. The method of claim 1, wherein the microorganism is a fungal microorganism.

9. The method claim of 1, wherein the microorganism is a drug resistant *Candida*.

10. The method of claim 1, wherein the polyphyllin D is naturally occurring.

11. The method of claim 1, wherein the polyphyllin D is chemically synthesized.

* * * * *